United States Patent [19]

Carpenter et al.

[11] Patent Number: 5,052,394

[45] Date of Patent: Oct. 1, 1991

[54] METHOD AND APPARATUS FOR ULTRASONIC BEAM COMPENSATION

[75] Inventors: David A. Carpenter, Northbridge; George Kossoff, Killara, both of Australia

[73] Assignee: Commonwealth Scientific and Industrial Research Organization, Campbell, Australia

[21] Appl. No.: 328,082

[22] PCT Filed: Jun. 10, 1988

[86] PCT No.: PCT/AU88/00181

§ 371 Date: Mar. 28, 1989

§ 102(e) Date: Mar. 28, 1989

[87] PCT Pub. No.: WO88/09939

PCT Pub. Date: Dec. 15, 1988

[51] Int. Cl.$^5$ .............................................. A61B 8/00
[52] U.S. Cl. .................... 128/660.06; 73/597; 73/599
[58] Field of Search ............... 128/660.01, 660.06, 128/660.10; 73/597, 599, 602, 625–626

[56] References Cited

U.S. PATENT DOCUMENTS

| | | | |
|---|---|---|---|
| 4,395,909 | 8/1983 | Steinberg et al. | 73/602 |
| 4,442,713 | 4/1984 | Wilson et al. | 128/660.06 X |
| 4,471,785 | 9/1984 | Wilson et al. | 73/602 X |
| 4,509,524 | 4/1985 | Miwa | 73/599 X |
| 4,566,459 | 1/1986 | Umemura et al. | 73/597 X |
| 4,733,668 | 3/1988 | Torrence | 128/660.01 |

Primary Examiner—Francis Jaworski
Attorney, Agent, or Firm—Ladas & Parry

[57] ABSTRACT

In ultrasonic echoscopy, when an object to be examined has overlying layers of a medium (for example, fat, muscle, skin or bone) which have different ultrasonic transmission characteristics from those of the object, the echogram of the object is usually distorted. To reduce that distortion, the present invention uses a transducer comprising an array of ultrasonic transducer elements operated in a higher resolution mode than its normal imaging mode, to obtain information about the geometry of the overlying layers. Using this information and a knowledge of the transmission characteristics of the overlying layers, amplitude and phase corrections are calculated, to enable the transducer, when operated in its normal imaging mode, to generate a required beam of ultrasound. The corrections are then applied and an echogram of the object, with reduced distortion, is obtained while operating the transducer in its normal imaging mode.

7 Claims, 3 Drawing Sheets

METHOD AND APPARATUS FOR ULTRASONIC BEAM COMPENSATION

TECHNICAL FIELD

This invention concerns ultrasonic echoscopy. More particularly, it concerns a technique and apparatus for rectifying the degradation of a beam of ultrasonic energy (ultrasound) as it passes through layers of different media before reaching the object that is being examined. Use of the invention will enable a significant improvement in a) cross-sectional ultrasonic images of the object being examined;
b) the accuracy of measurement of parameters such as attenuation and speed of propagation of ultrasound in human tissue using tissue characterisation techniques;
c) the accuracy of measuring liquid flow in vessels using the ultrasonic Doppler technique; and
d) the production of images and the taking of measurements within the object being examined when through transmission techniques are being used.

The invention is particularly, but not solely, directed to the use of ultrasonic echoscopy techniques in medical diagnostic examination.

BACKGROUND ART

Ultrasonic echoscopy provides information about an examined object which may be displayed in the form of an ultrasonic echogram. Such an echogram consists of a display of acoustic impedance discontinuities or reflecting surfaces in the object. It is obtained by directing a short pulse of ultrasonic energy, typically having a frequency in the range of from 1 to 30 MHz, into the object being examined. Any acoustic impedance discontinuities in the object reflect and return some of the energy in the form of an echo. This echo is received, converted into an electrical signal and displayed as an echogram on a cathode ray oscilloscope, a film, a chart or the like.

The echogram may constitute a one dimensional (A-mode) or a two dimensional (B-mode) representation of the object being examined. In both cases, the information is contained in the position and magnitude of the echo displayed. In a one dimensional display, the position along a base line is used to indicate the distance to the reflecting surface whilst the magnitude of the echo is displayed, for example, as a deflection of the base line or as an intensity change. In a two dimensional display, the position along a base line is used to indicate the distance to the reflecting surface (as in a one dimensional display) and the direction of the base line is used to represent the direction of propagation of the acoustic energy. The two dimensional display is obtained by changing this direction of propagation of the acoustic energy and by instituting a similar, but not necessarily identical, movement of the base line of the display. The magnitude of the echo is displayed as for a one dimensional display, for example, as a deflection of the base line or—more usually—as an intensity change.

The technique of ultrasonic echoscopy used in medical diagnosis to obtain information about the anatomy of patients has been widely reported. It has proved of particular value as a diagnostic aid when examining the abdomen and uterus, eye, breast, lung, kidney, liver and heart, these being regions of soft tissue with little bone and air. In general, the technique is considered to compliment other techniques to provide a more complete picture of a patient's condition. However, particularly in pregnancies, ultrasonic echoscopy may be useful in place of x-rays where the latter may not give sufficient information or may be dangerous. In such medical applications, a pulse of ultrasonic energy is transmitted into a patient in a known direction and echoes are received from reflecting surfaces within the body. The time delay between the transmission of a pulse and the reception of an echo depends on the distance from the transmitting ultrasonic transducer to the reflecting surface. The distance information so obtained may be displayed for interpretation and clinical use as a one dimensional range reading or as a two dimensional cross section, as previously described.

It is known (see, for example, the specification of U.S. Pat. No. 3,939,707 to Kossoff) to measure blood flow in the body along an ultrasonic line of sight by measuring the frequency shift of ultrasonic echoes and combining the frequency shift data with blood vessel dimensional and directional information that has been obtained from the B-mode ultrasonic echogram of the area. Using this technique, an absolute measurement of the blood flow is obtained.

It is assumed in the simple application of the pulse echo principle that a pulse of ultrasonic energy propagates through the various media of an object at a uniform velocity of propagation. In soft tissues in a human body, this velocity of propagation is of the order of 1570 meters per second (m/s). However, a scanning beam of ultrasound will suffer distortion as it propagates through media having different characteristics from those of the soft tissue being examined. The distortion is due to refraction, which is a consequence of the different velocity of propagation in each medium, and attenuation (which is due to a number of effects, including reflection at the interfaces between media and scattering). The distortion is manifest as an unclear or inaccurate echogram of the object being examined, and in deviation of the beam from its initial line of sight, widening of the beam and an increase in the level of the sidelobes of the transmitted signal.

It has long been recognised that the removal of these distortions will give an improvement in the resolution and clarity of the resulting echograms. An improvement in the beam quality will also improve the accuracy of tissue characterisation measurements and will improve the signal to noise ratio for the ultrasonic Doppler technique used to measure blood flow.

DISCLOSURE OF THE PRESENT INVENTION

It is an objective of the present invention to provide a method and apparatus which can be used to reduce the distortions, due to refraction and attenuation suffered by a beam of ultrasonic energy, and thus provide improved echograms and improved measurements of tissue characteristics and blood flow.

This objective is achieved by measuring the geometries of different media overlying the region of interest in the body being examined, and then using this information, and the known velocity of propagation of ultrasound in such media, to construct a correctly focused beam of ultrasound for use in the region of interest.

In the human body, for example, most organs are located behind overlying tissues which are primarily skin, muscle and fat. Each of these has a propagation velocity for ultrasound which is significantly different from the normal velocity of propagation in the internal organs, which is about 1570 m/s. In skin, the velocity of propagation of ultrasound is about 1750 m/s, in muscle it is about 1620 m/s, and in fat it is about 1440 m/s. The attenuation of ultrasonic energy is also different in these media, with muscle being more attenuating than fat. The practice of the present invention involves the measurement of the geometry of the layers of skin, muscle and fat (typically using high frequency ultrasound). From this measurement of the thicknesses and shapes of these layers, and with an a priori knowledge of ultrasound propagation velocities and attenuations, it is possible to compute the required ultrasound beam corrections in terms of time delays and signal levels. These time delays and signal levels are then used to construct a correctly focused beam of ultrasonic energy to propagate deeper into the body, hence removing the distortions due to the overlying layers.

The measurement of overlying layers can be achieved using an array of ultrasonic transducer elements operated to achieve a high resolution measurement of the object(s) being examined. There are a number of known techniques which may be used to improve the depth resolution of an ultrasound system, usually at the expense of sensitivity or penetration depth in tissue (which is unimportant in the present situation since only the geometry of the overlying or superficial layers is being measured). Those techniques include (this list is not exhaustive):

a) additional mechanical loading on the elements of the array via changes in the backing layers and/or the matching layers;
b) changes to the electrical matching and loading of the elements;
c) signal processing changes to give shorter pulses on transmission and/or reception of signals; and
d) the operation of the array at a higher frequency (such as, at the frequency of the third or fifth overtone).

The measurement of the geometry of the overlying layers can also be performed using a single ultrasonic transducer element, independently or in such an array, or using any number of elements in such an array less than the full array.

After applying the necessary corrections, a beam of ultrasound generated in the normal imaging mode by the array is used to obtain an echogram of the deeper internal structure(s) being investigated.

Thus, according to the present invention, there is provided a method of generating a beam of ultrasonic energy for obtaining an echogram of an object over which there is at least one layer of a medium having different ultrasonic transmission characteristics from those of the object, said method comprising the steps of a) positioning an ultrasonic transducer for examination of the object, the ultrasonic transducer including an array of ultrasonic transducer elements and being adapted to generate beams of ultrasound at a fundamental frequency (usually at 3.5 MHz);
b) operating the transducer in a higher resolution mode, in which at least one of the transducer elements is operated at a frequency which is higher than said fundamental frequency, to obtain information about the geometry of the medium or media interposed between the transducer and the object;
c) calculating, using a knowledge of the ultrasonic transmission characteristics of the medium or media and the geometrical information obtained by step (b), the amplitude and phase corrections to be applied to the transducer elements of the transducer to generate a required beam of ultrasonic energy within the object; and
d) generating a beam of ultrasonic energy from the transducer by operating the transducer at said fundamental frequency and applying the corrections calculated by step (c) to the phase and amplitude of the electrical pulses applied to activate the elements of the array.

As noted already, one method for obtaining higher resolution is to operate the transducer at a harmonic of the fundamental frequency.

The present invention also encompasses apparatus for generating a beam of ultrasonic energy for obtaining an echogram of an object over which there is at least one layer of a medium having different ultrasonic transmission characteristics from those of the object, said apparatus comprising:

a) an array of ultrasonic transducer elements, each transducer element being adapted to transmit ultrasound into the object when activated and to receive reflected echoes of the ultrasound from the object;
b) means to operate the array of transducer elements at a higher resolution mode than its normal imaging mode, to obtain information about the geometry of the or each overlying layer; and
c) means including a clock and delay lines to modify the normal activation of the elements of the array when the array is used in its normal imaging mode to apply a correction to the beam of ultrasound generated by the array, calculated on the basis of the information obtained about the geometry of the overlying layer or layers, to reduce the distortion of the echogram image of the object obtained using the array.

An embodiment of the present invention will now be described, by way of example only, with reference to the accompanying drawings.

DETAILED DESCRIPTION OF THE ILLUSTRATED EMBODIMENT

Figure 1:
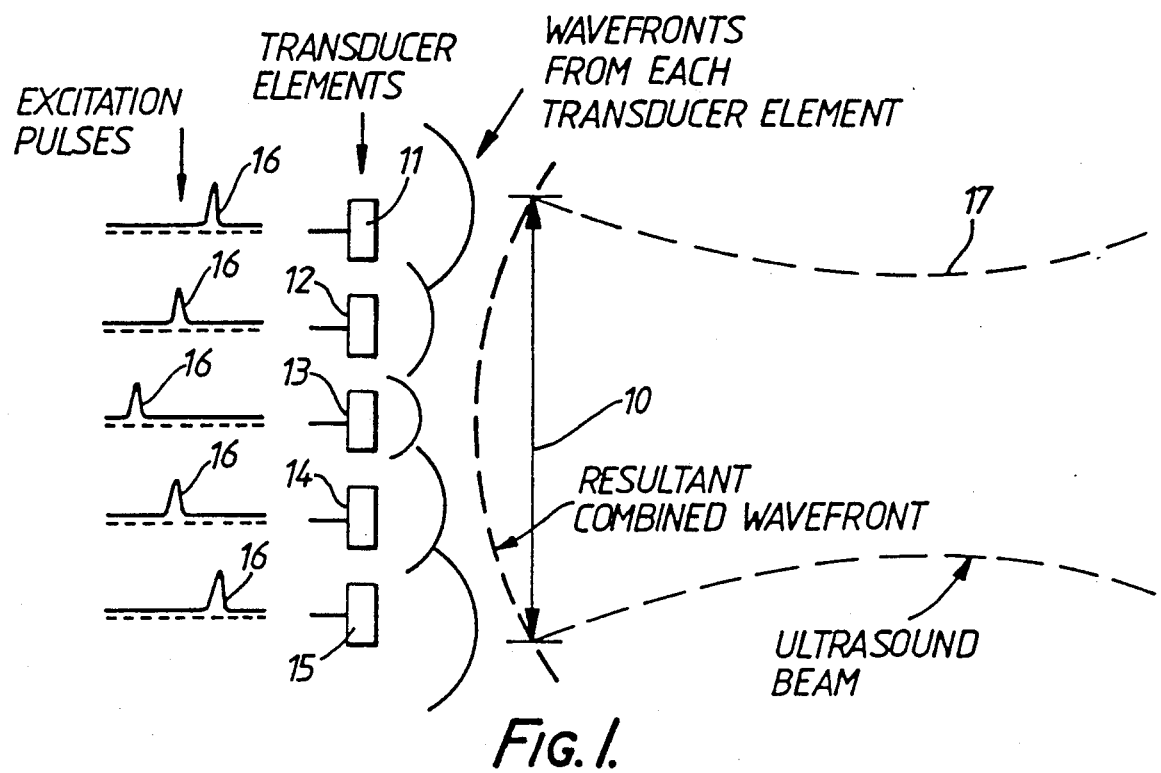
FIG. 1 illustrates, schematically, the generation of a focused beam of ultrasonic energy by exciting an array of transducer elements, as is known in this art.

It is common practice in modern medical ultrasonic imaging (also in radar and sonar imaging) to generate the imaging beam using an array of transducer elements. In the arrangement shown in FIG. 1, each of five ultrasonic transducer elements 11, 12, 13, 14 and 15 contributes to part of the overall aperture 10 used to transmit a beam 17 of ultrasonic energy. Similarly, these transducer elements make up the total aperture used to receive the beam reflected from the target.

Figure 2:
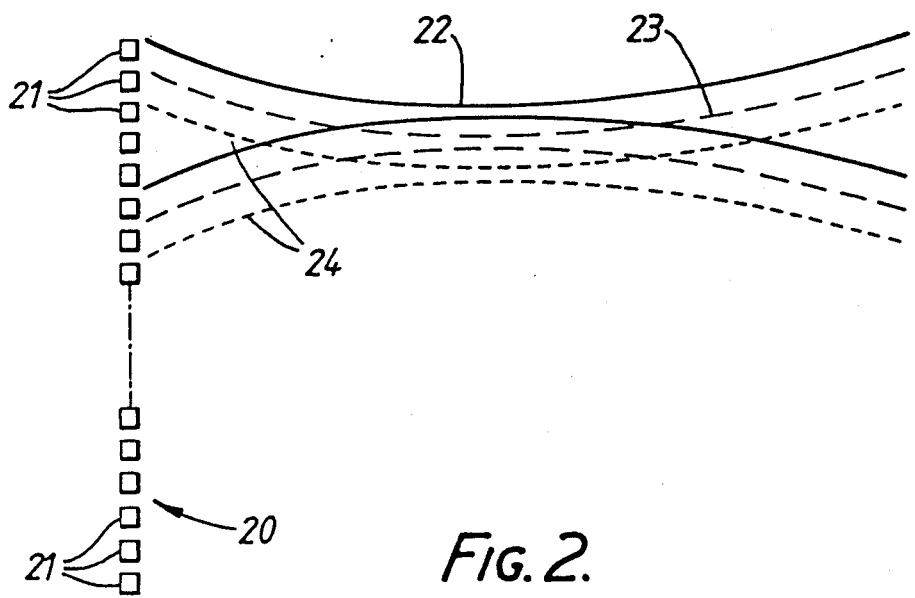
FIG. 2 shows the operation of a long linear array transducer which provides a linear scan of an area of interest, also as known in this art.

The linear array scanner illustrated in FIG. 2 consists of an array 20 of transducer elements 21 which sends out a focused beam of ultrasound at right angles to the transducer face. The beam is focused by applying time delays to the energising pulses as they are sent to the array elements to produce the transmitted beam. Such energising pulses are referenced 16 in FIG. 1. Similarly, time delays are applied to the signals received on the transducer elements 21 to produce a focused beam on reception. The beam is scanned over the area of interest by switching to another group of elements for each new line of sight. For example in the array of FIG. 2, beam 22 is formed by the first five elements in the array, beam 23 is formed by the second to sixth elements, beam 24 is created by the third to seventh elements, and so on along the transducer array.

Figure 3:
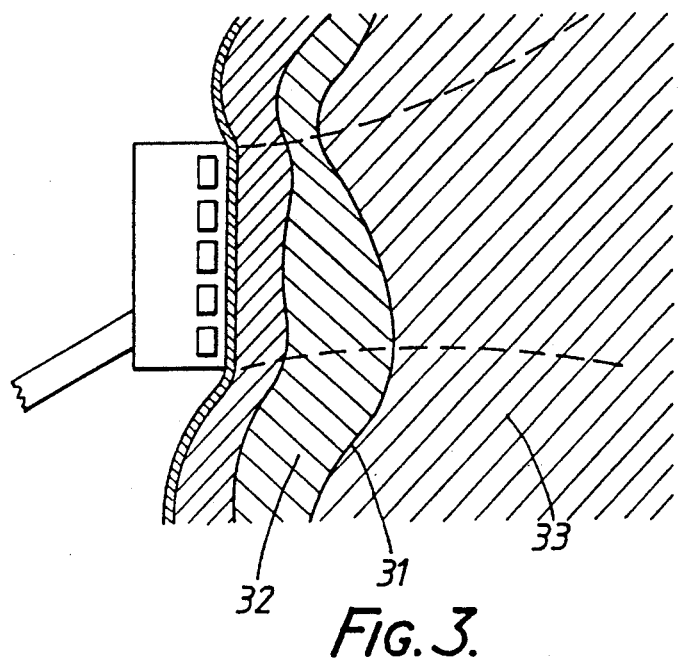
FIG. 3 is a schematic sectional view of part of the human body, showing a typical distribution of the layers of media, with an ultrasonic transducer applied to the body and ultrasound beam dispersion occurring at the interface between an overlying region of muscle and an internal organ.

In the present invention, the linear array forming the transducer may need to be modified, as noted above, to operate in a higher resolution mode, to measure the overlying layers. In the following description of the illustrative embodiment, it will be assumed that the array is to be operated at a higher frequency to increase the measurement resolution. Thus, if the array of elements 11, 12, 13, 14 and 15 of the array 20, is a 3.5 MHz array, the transducer elements may be excited at 10.5 MHz (the third overtone of 3.5 MHz). The beam of ultrasound produced at this higher frequency is used to measure the distance to the interface between the overlying tissues and an organ of soft tissue that is being examined. In the example given in FIG. 3, this high frequency operation gives high resolution images of the interface 31 between the muscle tissue layer 32 and the liver 33.

The frequency of operation for imaging should be as high as possible for good resolution. However, the attenuation of ultrasound by tissue is proportional to the frequency of the ultrasound, and a maximum frequency exists for each required penetration depth. Since the interfaces are at a close range, a considerably higher frequency can be used, thus affording a better range resolution for the measurement of layer thickness. As noted above, the high frequency mode of operation may use the normal set of ultrasonic transducer elements used for imaging or a subset of the elements, with different degrees of focusing, in order to obtain the optimum resolution in measuring the geometry of the overlying layers.

Having obtained a high resolution measurement of the distribution of the layers overlying the organ of interest using the high frequency higher resolution mode (or any of the other known higher resolution procedures), the required velocities and amplitude variations to correct the ultrasound beam characteristics when operating in the normal imaging mode can be assigned.

It is necessary to translate the image corrections into time differences to be imparted to various parts of the beam, and to compute the difference in time delay which must be imparted to the activating signal of each transducer element in the array of transducer elements which generates the transmitted ultrasound beam and receives the echoes from acoustic discontinuities, to compensate for the different propagation velocities in the tissue layers along a particular line of sight. Similarly it is necessary to compensate for the different attenuations experienced by different parts of the beam.

Figure 4:
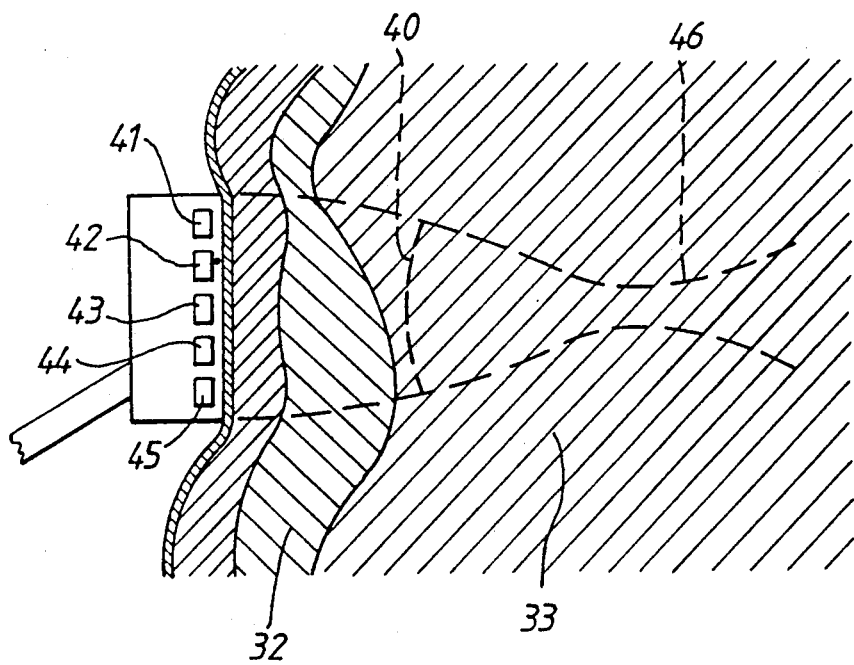
FIG. 4 is a similar view to FIG. 3, but with the ultrasound beam corrections applied.

In the situation depicted in FIG. 4, the contributions to the beam of ultrasonic energy which are provided by the elements 41 and 42 propagate through less muscle 32 than the contributions from the elements 43, 44 and 45. Hence the contribution to the ultrasound beam from the transducer elements 41 and 42 is attenuated less and refracted more due to the higher propagation velocity in the muscle 32. This can be corrected by applying additional gain to the signal transmitted (and received) by the transducer elements 43, 44 and 45 and extra time delays to the signals used to activate the elements 41 and 42, so that by the time the beam enters the liver 33, the element contributions will be of the correct amplitude and in the correct phases to produce a focused wavefront 40 and hence a focused beam 46. With these new amplitude and time delays set, the linear array can be operated along this line of sight at its fundamental frequency (typically 3.5 MHz when imaging a human abdomen).

If there are two or more interfaces (for example, a fat and muscle interface followed by a muscle and organ interface), this process can be repeated a number of times to compensate for distortions due to the multiple media layers.

The correction process has to be repeated for each line of sight along the linear array scan to obtain a good image of the area of interest in the deeper structures. The correction process also has to be repeated for each line of sight along different locations of the array in the plane perpendicular to the paper containing FIGS. 3 and 4, if multiple echograms are required, for the thickness of the overlying tissue varies in two dimensions.

As the measurement and compensation process described above can be carried out quickly by the modified scanner, the imaging can proceed at close to real time scanning speeds. The frame rate of a real-time imaging system is dependent on the time required for the desired number of ultrasonic pulses to propagate twice through the maximum depth of tissue (that is, once to travel into the tissue and once to return to the transducer). The high resolution measurement step requires additional time but since the maximum depth of penetration for the overlying layers is small, the additional time is small and the overall increase in scanning time is low.

Figure 5:
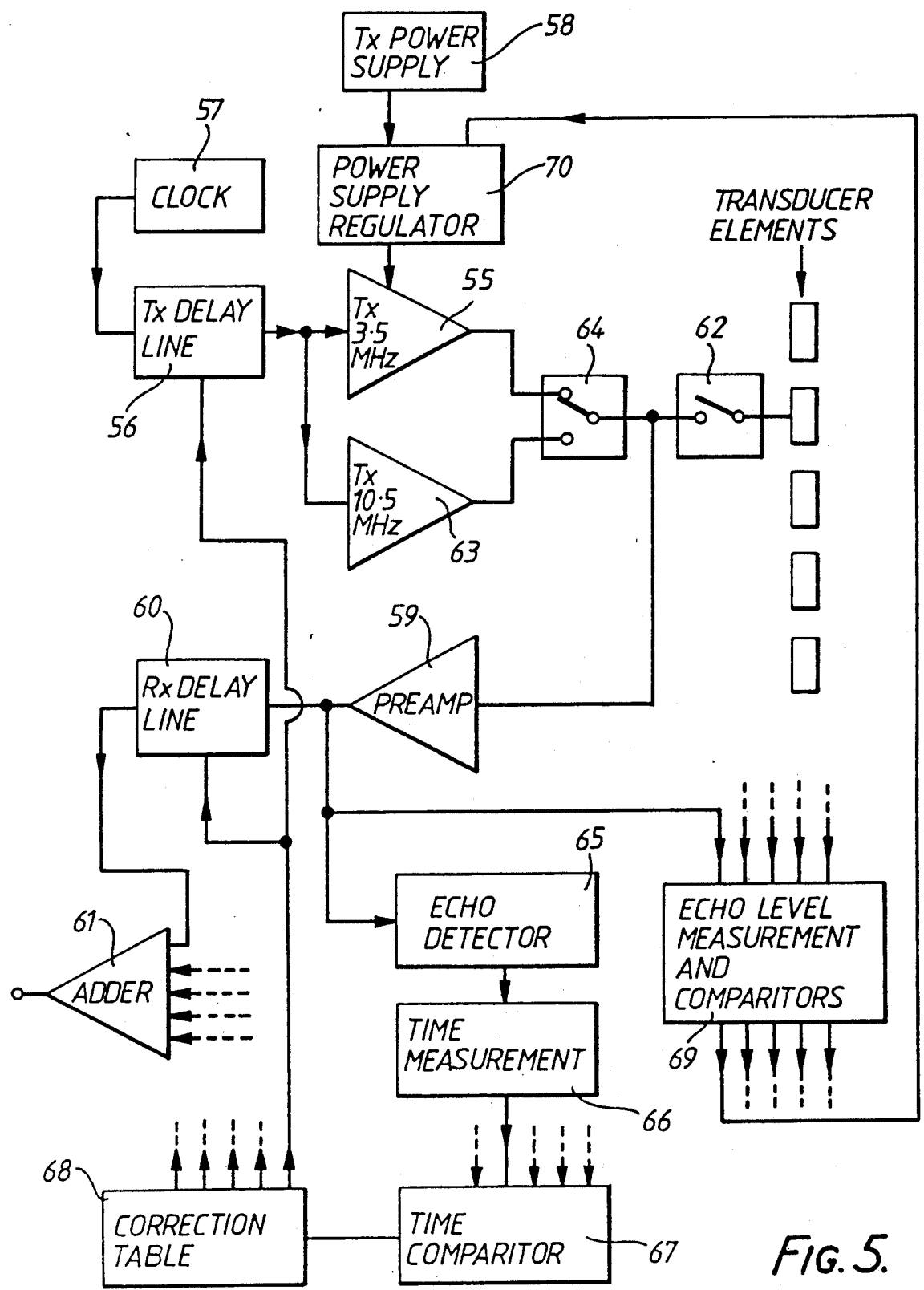
FIG. 5 is a block diagram of a modified linear array scanner that may be used to practice the present invention.

FIG. 5 shows a partial block diagram of the apparatus needed to perform the invention. The diagram shows the circuitry needed for one element in the aperture. In the case of the transducer shown in FIGS. 1 and 2, where five transducer elements are used for each beam of ultrasonic energy, most of this circuitry would have to be repeated five times. The exceptions are the clock 57, the transmitter power supply 58, the adder 61, the time comparator 67, the correction table 58 and the echo level measurement and comparator circuitry 69, which are common to all transducer elements in the aperture. The following components are basic to the operation of a linear array ultrasonic scanner and are well known in the ultrasonic echoscopy art:

a) the transmitter circuit 55 used to excite the array element at its fundamental frequency (usually 3.5 MHz);

b) the transmit delay circuit 56 used to time the excitation of the elements to produce a focused transmit beam;

c) the clock circuit 57 which produces the timing of transmit pulses for the scanner;

d) the transmit power supply 58 that is used to set the output level of the scanner;

e) the preamplifier 59 that operates to increase the echo level received on the transducer element;

f) the receive delay line 60 used to set the timing of the returned echoes to produce a focused receive beam;

g) the adder 61 which combines the signals from all the receive elements; and h) the switch 62 which connects the elements of the array needed to form a particular beam to the appropriate electronics.

The switch 62 may connect different elements or combinations of elements into the system when it is being used in the higher resolution mode to measure the geometry of the overlying layers from when the system is being used for normal imaging of an object.

The following are the additional circuits that are needed to carry out the method of the present invention:

i) the higher resolution transmitter 63 (which, in the implementation described above, operates at a frequency of 10.5 MHz);

j) the switch 64 between the fundamental frequency transmitter 55 and the higher resolution transmitter 63;

k) an echo detector circuit 65 to detect the echoes from the overlying tissue layers in the higher resolution measurement mode of operation;

l) a time measurement circuit 66 which measures the time between the transmit pulse and the echoes from the overlying layers;

m) a time comparator circuit 67 that is used to compare the times measured in the time measurement circuit 66 between each of the elements used in the aperture to form the beam;

n) a correction table circuit 68 which uses the times measured in the time comparator circuit 67 to set the correct values of the transmit delays provided by the delay line 56 and the receive delays provided by the receive delay line 60, to give the correctly compensated focused beam within the body (this can be implemented by computing the corrected time delays or by using a look-up table of corrected times);

o) an echo level measurement and comparator circuit 69 to measure the echo level received on each element from the interface of the overlying tissue layer and, by comparing levels between elements, to set the correct transmit voltage levels for each element, thus ensuring that each transducer element in the aperture will contribute the correct level to form the compensated focused beam within the body; and p) a transmit voltage regulator circuit 70 to allow the levels set by the echo level measurement circuit 69 to adjust the voltage applied to the fundamental frequency transmitter 55.

With this identification of the circuit components, the operation of the arrangement illustrated in FIG. 5 will be self-evident to persons of skill in this art.

Those skilled in this art will also appreciate that although a specific form of the present invention has been illustrated and described above, modifications thereto may be made without departing from the present inventive concept. For example, as indicated earlier, different types of transducer arrays may be used. In particular, each linear array of transducer elements that has been included in the illustrated embodiment of the apparatus of this invention may be replaced with an arcuate array of transducer elements, which performs a mechanical pre-focusing of the ultrasound beam. In such an arrangement, the position of the focus of the beam is adjusted by varying the phase of the actuating excitation pulses supplied to the individual transducer elements in the array. Also, although a transducer having an array of five transducer elements has been illustrated in FIGS. 1, 3 and 4, any suitable number of transducer elements may be included in an array. And, as indicated earlier in this specification, any of the alternative known techniques for achieving higher resolution of the images of the overlying layers may be used instead of the higher frequency operating mode of the ultrasonic transducer.

We claim:

1. A method of generating a beam of ultrasonic energy for obtaining an echogram of an object over which there is at least one layer of a medium having different ultrasonic transmission characteristics from those of the object, said method comprising these steps of
    (a) positioning an ultrasonic transducer for examination of the object, the ultrasonic transducer including an array of ultrasonic transducer elements and being adapted to generate beams of ultrasound at a fundamental frequency;
    (b) operating the transducer in a higher resolution mode, in which at least one of the transducer elements is operated at a frequency which is higher than said fundamental frequency, to obtain information about the geometry of the medium or media interposed between the transducer and the object;
    (c) calculating, using a knowledge of the ultrasonic transmission characteristics of the medium or media and the geometrical information obtained by step (b), the amplitude and phase correction to be applied to the transducer elements of the transducer to generate a required beam of ultrasonic energy at said fundamental frequency within the object; and
    (d) generating a beam of ultrasonic energy from the transducer by operating the transducer at said fundamental frequency and applying the corrections calculated by steps (c) to the phase amplitude of the electrical pulses applied to activate the elements of the array.

2. A method as defined in claim 1, in which the frequency used in said higher resolution mode of said transducer which is higher than said fundamental frequency is an overtone of said fundamental frequency.

3. A method as defined in claim 2, in which said object is a blood-carrying vessel and said method includes the additional step of measuring the doppler frequency shift of the echoes from said vessel when operating said transducer in its normal imaging mode in step (d).

4. A method as defined in claim 1, in which said object is a blood-carrying vessel and said method includes the additional step of measuring the doppler frequency shift of the echoes from said vessel when operating said transducer in its normal imaging mode in step (d).

5. Apparatus for generating a beam of ultrasonic energy for obtaining an echogram of an object over which there is at least one layer of a medium having different ultrasonic transmission characteristics from those of the object, said apparatus comprising:
    a) An array of ultrasonic transducer elements, each transducer element being adapted to transmit ultrasound into the object when activated and to receive reflected echoes of the ultrasound from the object;

b) means to operate the array of transducer elements at a higher resolution mode than its normal imaging mode, to obtain information about the geometry of the or each overlying layer; and c) means including a clock and delay lines to modify the normal activation of the elements of the array when the array is used in its normal imaging mode to apply a correction to the beam of ultrasound generated by the array, calculated on the basis of the information obtained about the geometry of the overlying layer or layers, to reduce the distortion of the echogram image of the object obtained using the array.

6. Apparatus as defined in claim 5, in which said means to operate the array of transducer elements at a higher resolution mode comprises means to operate at least one of the transducer elements at a frequency which is an overtone frequency of the fundamental frequency of operation of the array.

7. Apparatus as defined in claim 5, including means to measure the doppler frequency shift of the echoes from the object when the object is a blood-carrying vessel.

* * * * *